United States Patent [19]
Harreld et al.

[11] Patent Number: 5,219,356
[45] Date of Patent: Jun. 15, 1993

[54] DISPOSABLE TOURNIQUET

[75] Inventors: Donald R. Harreld, Woodstock; Barbara T. Skiba, Chicago, both of Ill.

[73] Assignee: Sage Products, Inc., Crystal Lake, Ill.

[21] Appl. No.: 839,371

[22] Filed: Feb. 21, 1992

[51] Int. Cl.⁵ .............................................. A61B 17/12
[52] U.S. Cl. ................................................... 606/203
[58] Field of Search ................................ 606/201-204; 128/686, 677, DIG. 26; 604/179, 180; 24/16 R, 16 PB, 17 R, 17 AP, DIG. 11, DIG. 16; 602/62, 57, 75, 903

[56] References Cited

U.S. PATENT DOCUMENTS

| | | | |
|---|---|---|---|
| 2,561,894 | 7/1951 | Wallich | 24/DIG. 11 |
| 3,086,529 | 4/1963 | Munz et al. | 606/203 |
| 3,376,865 | 4/1968 | Gamper | 606/201 |
| 3,504,675 | 4/1970 | Bishop, Jr. | |
| 3,930,506 | 1/1976 | Overend . | |

FOREIGN PATENT DOCUMENTS 2035607  1/1972  Fed. Rep. of Germany ...... 606/203

Primary Examiner—John D. Yasko
Assistant Examiner—William Lewis
Attorney, Agent, or Firm—Lee, Mann, Smith, McWilliams, Sweeney & Ohlson

[57] ABSTRACT

A disposable tourniquet comprising an elongated, flat, stretchable band. The band has a pressure-sensitive adhesive face on one side of the band at one end, and a release agent on the same face of the band but spaced from the adhesive face. The tourniquet is stored with the adhesive face folded against and adhering to the release agent, and is deployed by peeling the adhesive face away from the release agent, wrapping the tourniquet about the arm and pulling it sufficiently tight, and then adhering the adhesive face to the outside surface of the band to hold the tourniquet in place.

9 Claims, 2 Drawing Sheets

U.S. Patent  June 15, 1993  Sheet 1 of 2  5,219,356
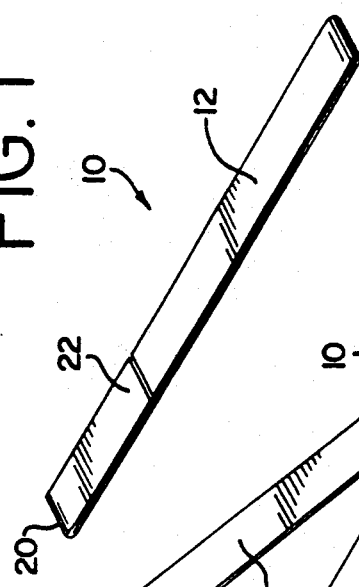
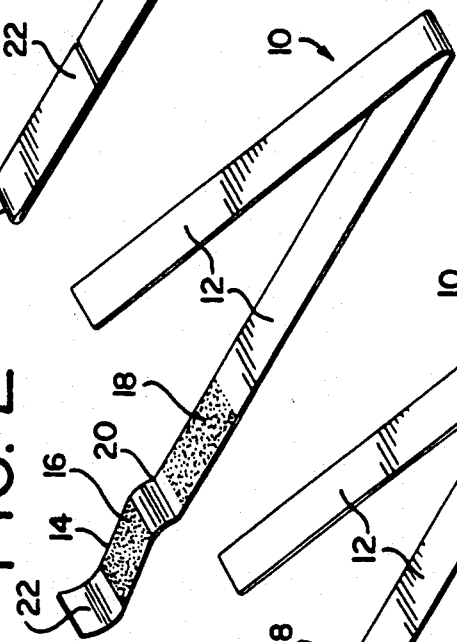
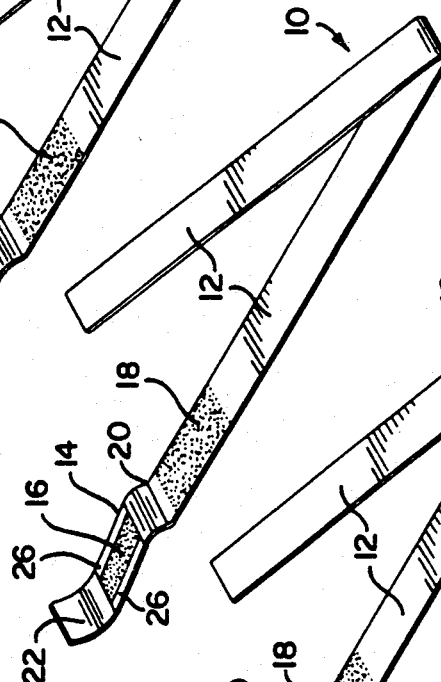
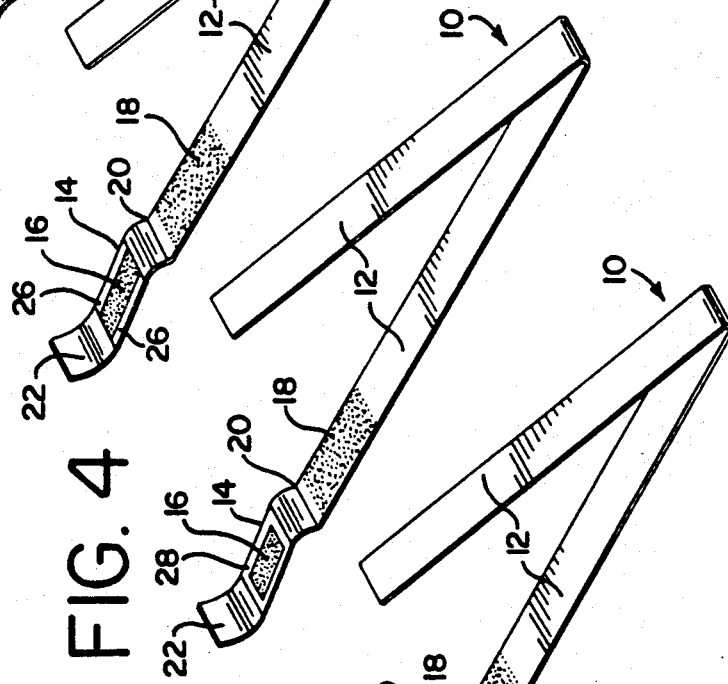
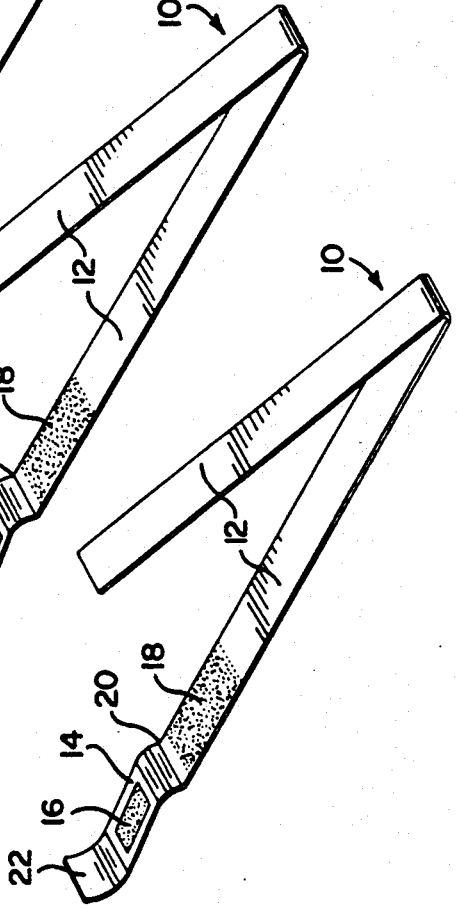

DISPOSABLE TOURNIQUET

BACKGROUND OF THE INVENTION

This invention relates to tourniquets, and in particular a disposable tourniquet which can be easily stored, readily deployed, and comprises only one piece when assembled.

Tourniquets are used on a patient's limbs for many purposes, but primarily to capture blood flow in a vein for removal of a sample and subsequent testing. Tourniquets run the gamut from lengths of cloth that are simply tied about a limb, elastic bands that are tied about a limb, or cloth strips having hook-and-loop fasteners for temporarily securing the strip in place about a patient's limb.

All such prior art devices share one common feature—they are all reusable, and are therefore susceptible to contamination. Since all such tourniquets are relatively expensive, it is prohibitively expensive to use the tourniquet one time and then dispose it. As a result, such tourniquets are used time and again, with the resultant risk of disease transmission.

U.S Pat. No. 3,930,506 discloses a disposable tourniquet made of a plastic band which has a pressure sensitive adhesive for adhering the two ends of the band to one another when drawn about a patient's arm. The adhesive is protected by a peel away liner which must be removed and discarded when the tourniquet is used. Thus, in addition to the disposable tourniquet, the doctor, nurse or other person using the tourniquet must be concerned with disposing of the protective liner. While the disposable tourniquet of this patent is a substantial improvement over non-disposable tourniquets, the peel away liner is a detriment.

SUMMARY OF THE INVENTION

The present invention is directed to a disposable tourniquet which comprises an elongated, flat, stretchable band. An adhesive strip is bonded to one side of the band on a first portion of the band adjacent one end of the band. The strip has a pressure-sensitive adhesive face having a predetermined length and a predetermined width. A release agent is applied to the same side of the band on a second portion thereof with the release agent being spaced from the adhesive strip. The release agent has a length at least as great as the length of the adhesive strip and a width also at least as great as the width of the adhesive strip. The tourniquet is oriented with the adhesive face releasably secured to the release agent with the first and second portions of the band facing one another such that the first portion can be separated from the second portion by peeling the adhesive face away from the release agent.

For orientation of the adhesive face toward the release agent when the tourniquet is stored, preferably the band has a transverse fold located between the adhesive strip and the release agent. The fold is positioned so that the distance from the fold to the adhesive face is at least as great as the distance from the fold to the release agent. In addition, the overall length of the release agent plus the distance from the fold to the release agent is at least as great as the length of the adhesive face plus the distance from the fold to the adhesive face. These relationships prevent the adhesive face from inadvertently being prematurely applied to the band.

In accordance with a preferred form of the invention, the adhesive strip is spaced from one end of the band, forming a tab to facilitate separation of the first and second portions when the adhesive face is releasably secured to the release agent. The tab can also be used as an aid when the tourniquet is wrapped about a limb.

In the primary form of the invention, the band has a particular width, and the width of the adhesive face is the same. In another form of the invention, the width of the adhesive face is narrower than the width of the band, and is spaced from opposite side edges of the band. In yet another form of the invention, the adhesive face spans the width of the band, but includes a mask overlying the face along opposite side edges of the band in order to narrow the effective width of the adhesive face.

The release agent can be a coating applied to the band, or can comprise a release strip adhesively attached to the band, with the release strip having a peel strength to the adhesive face of the adhesive strip being less than any peel strength of the release strip to the band itself. Therefore, whenever the tourniquet is deployed, the release strip remains in place and is not inadvertently peeled away while adhering to the adhesive face of the adhesive strip.

BRIEF DESCRIPTION OF THE DRAWINGS

The invention is described in greater detail in the following description of examples embodying the best mode of the invention, taken in conjunction with the drawing figures, in which:

FIG. 1 is a perspective view of a disposable tourniquet according to the invention, in its stored or undeployed orientation, FIG. 2 is a perspective view of the disposable tourniquet of FIG. 1, showing the tourniquet as it is being deployed, FIG. 3 is a view similar to FIG. 2, but showing a narrower adhesive face created by side masks, FIG. 4 is a view similar to FIG. 3, but with the adhesive also truncated in length by a surrounding mask, FIG. 5 is a view similar to FIG. 4, but without a mask and having simply a smaller area of adhesive.

DESCRIPTION OF EXAMPLES EMBODYING THE BEST MODE OF THE INVENTION

Figure 6:
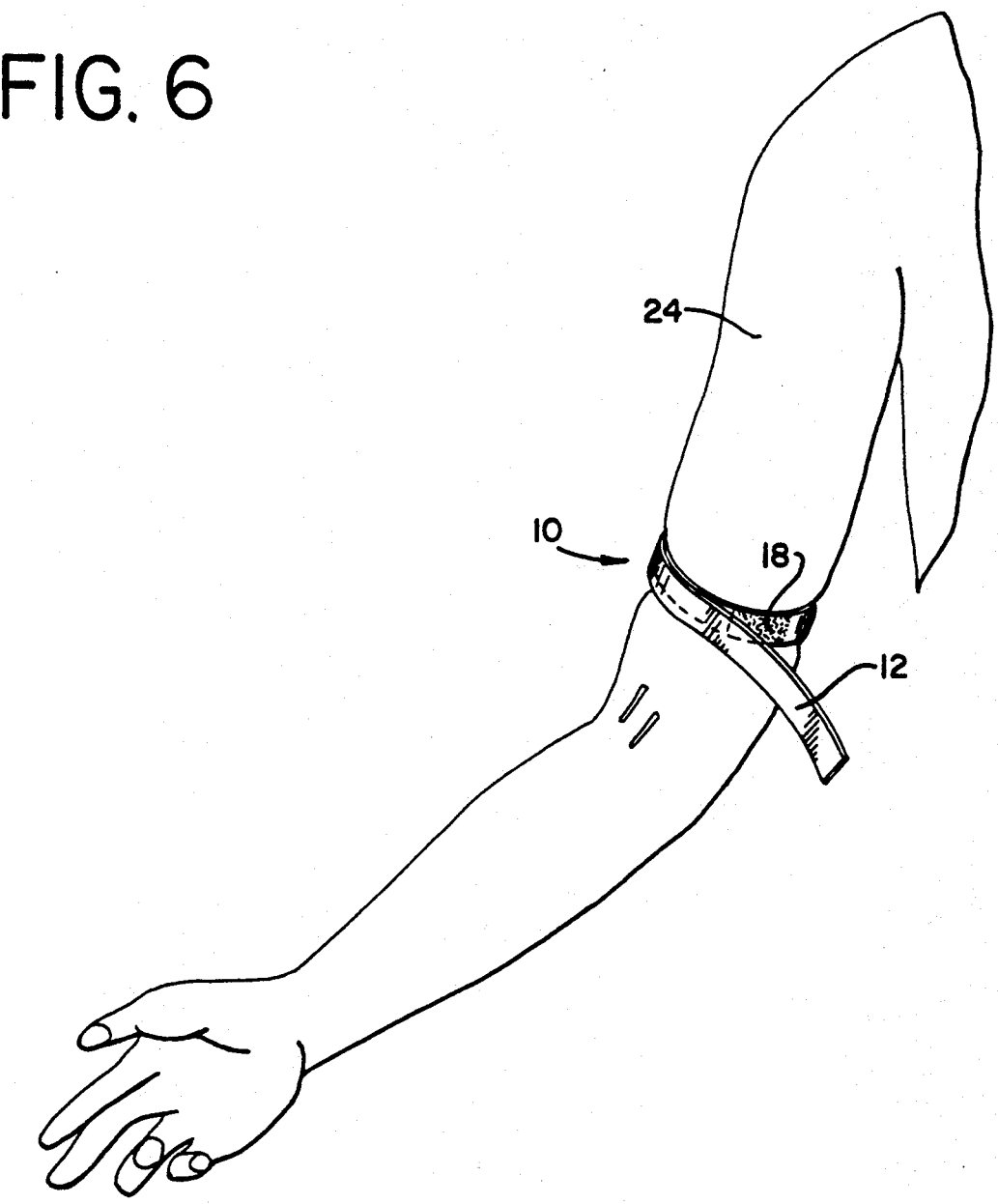
FIG. 6 is an elevational view showing a tourniquet according to the invention as applied to a patient's arm.

A disposable tourniquet according to the invention is shown generally at 10 in the drawing figures. The tourniquet comprises an elongated, flat, stretchable band 12, made of a suitable material, such as plastic.

An adhesive strip 14 is bonded to one side of the band 12 in an area or portion of the band adjacent one end thereof. The adhesive strip 14 includes a pressure-sensitive adhesive face 16 having a desired length and width. A release agent 18 is bonded to the same side of the band 12 on a second area or portion of the band spaced from the adhesive strip 14. So that the adhesive face 16 does not inadvertently and prematurely adhere to the band 12, the release agent 18 has a width at least as great as the width of the adhesive strip 14 and a length at least as great as the length of the adhesive strip 14. The release agent 18 may comprise a non-adhesive coating applied to the band 12, or, preferably, comprises a release strip adhesively attached to the band, with the release strip having a peel strength to the adhesive face 16 which is less than any peel strength of the release strip to the band 12. Thus, when the tourniquet 10 is deployed, the release strip comprising the release agent 18 remains in place as shown in FIGS. 2-5, and does not inadvertently adhere to the adhesive face 16.

A transverse fold 20 is provided in the band 12 between the adhesive strip 14 and the release agent 18. The fold orients the tourniquet 10 with the adhesive face 16 releasably secured to the release agent 18 before the tourniquet is used. The adhesive face 16 is simply peeled away from the release agent 18 when the tourniquet is used.

To facilitate use of the tourniquet, the adhesive strip 14 is spaced from the end of the band 12, forming a pull tab 22. For deploying the tourniquet, the pull tab is grasped in one hand while the tourniquet is held in the other, and is pulled to separate the adhesive face 16 from the release agent 18.

The tourniquet is used as shown schematically in FIG. 6. With the adhesive face 16 peeled away from the release agent 18, the band 12 is wrapped about a patient's arm 24 with the adhesive face 16 extending outwardly away from the patient's skin. The band 12 is stretched as required, and then adhered to itself by pressing the portion of the band overlying the adhesive face 16 into the adhesive face. The band is then held securely in place until blood work has been completed. For removal, the band 12 can be torn or, if the strength of the adhesive of the adhesive face 16 is sufficiently low, the band can be separated from the adhesive face to remove the tourniquet.

In the form of the invention shown in FIG. 2, the adhesive face 16 extends the width of the band 12. In some instances, it may be appropriate to have the adhesive face 16 be narrower. The narrower adhesive face has a lesser proclivity to adhere to other items, such as hair on a patient's arm. To this end, a pair of masks 26 are adhered to and overlie the adhesive face 16 along opposite side edges of the band 12. Thus, the width of the adhesive face 16 is effectively narrowed.

In other instances, it may be desired to both narrow and shorten the effective length of the adhesive face 16. As shown in FIG. 4, to achieve this end, the adhesive face 16 may be overlain by a mask 28 which extends about the periphery of the adhesive face 16, both at the sides and the ends of the adhesive face. Alternatively, as shown in FIG. 5, the adhesive face 16 may occupy less than the entire surface of the adhesive strip 14, accomplishing the same result.

Obviously, the length and width of the adhesive face 16 can be no greater than the length and width of the release agent 18, or a portion of the adhesive face 16 would prematurely adhere to part of the band 12 when the tourniquet 10 is stored in the orientation shown in FIG. 1. In addition, the distance from the fold 20 to the adhesive face 16 must be at least as great as the distance from the fold 20 to the release agent 18 to also preclude improper adherence of the adhesive face 16 to a portion of the band 12. Finally, the length of the release agent 18 plus the distance from the fold 2 to the release agent 18 must also be at least as great as the length of the adhesive face 16 plus the distance that the adhesive face 16 is spaced from the fold 20.

The adhesive face 16 is preferably applied to an adhesive strip 14 which is then bonded to the band 12. The adhesive strip 14, in combination with the material of the band 12, resists stretching of the band beneath the adhesive face 16, and therefore undesired stretching or deformation of the adhesive face 16. Alternatively, however, the adhesive face 16 can be applied directly to the band 12 without an intervening strip or other material. Various changes can be made to the invention without departing from the spirit thereof or scope of the following claims.

What is claimed is:

1. A disposable tourniquet, comprising:
   a. an elongated, flat, stretchable band,
   b. an adhesive strip bonded to one side of said band on a first portion of said band adjacent one end of said band, said strip having a pressure-sensitive adhesive face having a predetermined length and a predetermined width,
   c. a release agent applied to said one side on a second portion of said band with said release agent being spaced from said adhesive strip, said release agent having a length at least as great as said predetermined length and a width at least as great as said predetermined width, said release agent extending along its length on said second portion, and
   d. means orienting said tourniquet with said adhesive face releasably secured to said release agent with said portions facing one another such that said first portion can be separated from said second portion by peeling said adhesive face away from said release agent.

2. A disposable tourniquet according to claim 1 in which said orienting means comprises a transverse fold in said band between said adhesive strip and said release agent.

3. A disposable tourniquet according to claim 2 in which said fold is positioned so that the distance from said fold to said adhesive face is at least as great as the distance from said fold to said release agent.

4. A disposable tourniquet according to claim 3 in which the length of said release agent plus the distance from said fold to said release agent is at least as great as said predetermined length plus the distance from said fold to said adhesive face.

5. A disposable tourniquet according to claim 1 in which said strip is spaced from said one end, forming a tab in said one end to facilitate separation of said first and second portions.

6. A disposable tourniquet according to claim 1 in which said band has a particular width, and said predetermined width is less than said particular width.

7. A disposable tourniquet according to claim 6 in which said adhesive face is spaced from opposite side edges of said band.

8. A disposable tourniquet according to claim 1 in which said band has a particular width and said predetermined width essentially equals said particular width, and including a mask overlying said adhesive face along opposite side edges of said band.

9. A disposable tourniquet according to claim 1 in which said release agent comprises a release strip adhesively attached to said band, said release strip having a peel strength to said adhesive face less than any peel strength of said release strip to said band.

* * * * *